(12) United States Patent
Bohlin et al.

(10) Patent No.: US 7,462,686 B2
(45) Date of Patent: Dec. 9, 2008

(54) ON-GROWTH INHIBITING COMPOUNDS

(75) Inventors: Lars Bohlin, Uppsala (SE); Martin Sjogren, Stromstad (SE); Per Claeson, Uppsala (SE); Ulf Goransson, Queensland (AU); Erika Svangard, Uppsala (SE)

(73) Assignee: Viogard AB, Stocksund (SE)

( * ) Notice: Subject to any disclaimer, the term of this patent is extended or adjusted under 35 U.S.C. 154(b) by 0 days.

(21) Appl. No.: 10/539,637

(22) PCT Filed: Dec. 16, 2003

(86) PCT No.: PCT/SE03/01961

§ 371 (c)(1),
(2), (4) Date: Apr. 25, 2006

(87) PCT Pub. No.: WO2004/055044

PCT Pub. Date: Jul. 1, 2004

(65) Prior Publication Data
US 2007/0020344 A1 Jan. 25, 2007

(30) Foreign Application Priority Data
Dec. 16, 2002 (SE) .................................... 0203700

(51) Int. Cl.
*C07K 7/64* (2006.01)
*C07K 14/00* (2006.01)
*C07K 14/415* (2006.01)
(52) U.S. Cl. ..................................... 530/317
(58) Field of Classification Search ........................ None
See application file for complete search history.

(56) References Cited

U.S. PATENT DOCUMENTS

| | | | |
|---|---|---|---|
| 4,342,751 A | 8/1982 | Moore et al. | |
| 6,335,318 B1 | 1/2002 | Selsted et al. | |
| 6,777,388 B1 * | 8/2004 | Grasso et al. | 514/16 |
| 2002/0037260 A1 * | 3/2002 | Budny et al. | 424/49 |

FOREIGN PATENT DOCUMENTS

WO    WO 01/27147 A1 *  4/2001

OTHER PUBLICATIONS

Craik D. J., Daly N. L., Bond T., and Waine C. (1999) Plant cyclotides: a unique family of cyclic and knotted proteins that defines the cyclic cystine knot structural motif. Journal of Molecular Biology 294: 1327-1336.*
Bacteria Introduction from the Merck Manual.*
Peridontitis from the MayoClinic.com.*
Peridontitis from the Merck Manual.*
Rudinger J, Characteristics of the amino acids as components of a peptide hormone sequence, Peptide Hormones, JA Parsons, Ed., 1976, 1-7.*
Desiging Custom Peptides from Sigma Genosys (www.sigma-genosys.com/peptide_design.asp), Accessed Dec. 16, 2004, 1-2.*
Berendsen HJC, A Glimpse of the Holy Grail?, Science, 1998, 282: 642-643).*
Voet D and Voet JG, Biochemistry, Second Edition, John Wiley & Sons, Inc., 1995, 235-241.*
STN International, File CAPLUS, CAPLUS accession No. 2003:349308, Document No. 138:350024, Marine Biotechnology Institute, Japan "Cyclic peptides, heir manufacture from Haliclon extracts, and antibiofouling agents containing them"; & JP 2003128696.
PNAS, vol. 98, No. 19, Sep. 2001, Cameron Jennings et al, "Biosynthesis and Insecticidal Properties of Plant Cyclotides: The Cyclic Knotted Proteins From Oldenlandia Affinis", p. 10614, col. 1; abstract.
Trends in Biochemical Sciences, vol. 27, No. 3, 2002, Manuela Trabi et al, "Circular Proteins- No End in Sight" p. 133.
Letters in Peptide Science, vol. 8, 2002, David J. Craik et al, "Discovery and Structures of the Cyclotides: Novel Macrocyclic Peptides From Plants", abstract.
Ulf Goransson et al., "Seven Novel Macrocyclic Polypeptides from *Viola arvensis*", *J. Nat. Prod.* 1999, 62, 283-286.

* cited by examiner

*Primary Examiner*—Anish Gupta
*Assistant Examiner*—Julie Ha
(74) *Attorney, Agent, or Firm*—Young & Thompson

(57) ABSTRACT

An on-growth inhibiting agent, for the inhibition and/or prevention of on-growth of biological organisms on objects or living beings, includes at least one cyclotide, and a suitable carrier medium. A plant extract containing a mixture of cyclotides is also usable.

9 Claims, 4 Drawing Sheets

ON-GROWTH INHIBITING COMPOUNDS

The present invention relates to compounds, methods and agents, for preventing or inhibiting on-growth of living organisms on surfaces in general, e.g. on physical objects and/or living beings, such as barnacles on marine structures, microorganisms forming bio-films on e.g. medical equipment, and on living animals, such as fish in fish cultures.

BACKGROUND OF THE INVENTION AND PRIOR ART

The solution of the severe technical and economical problem caused by marine fouling organisms, e.g. barnacles, blue mussels, algae and hydroids, for the shipping industry and in aquaculture has been the use of TBTO (tri-n-butyl tin oxide), copper oxide and herbicides in marine coatings. However, several of these have been recognised to be toxic against non-fouling marine organisms. For example, TBTO has been ascribed effects such as reproduction failure and decrease in adult growth in oysters and the development of imposex in gastropodes such as the dog whelk. Because of these unwanted side effects, the use of TBTO will be stopped by future bans; the International Marine Organisation will recommend a global ban from the year 2005. Therefore it is urgent to find new non-toxic alternatives which exert a specific action on target organisms and which also are biodegradable.

Craik et al in WO 01/27147 discloses a novel cyclic molecular framework comprising i.a. so called cyclotides, i.e. cyclic peptides. These compounds are claimed to be usable for treatment or prophylaxis of disease conditions in animals, mammals and plants.

WO 00/68265 (Ouelette et al) discloses pharmaceutical compounds based on cyclic peptides.

WO 99/21879 (Chang et al) discloses cyclic peptides having antimicrobial and antibacterial activity.

SUMMARY OF THE INVENTION

I.a. in view of the toxicity of the presently used compounds for preventing on-growth on i.a. marine structures, it would be desirable to have access to nontoxic substances, which do not accumulate in the environment, and which do not intervene irreversibly in the natural biological/ecological systems.

One promising approach to find new non-toxic antifouling agents has been to explore natural compounds occurring in the marine environment, especially those produced by marine organisms free from fouling. The present inventors have shown that this search among biologically active natural products may be expanded to terrestrial ones as well, by the potent, antifouling effect against barnacles (*Balanus amphitrite*, Darwin) of the plant peptide cycloviolacin O2, isolated from the Sweet violet, *Viola odorata* L. (Violaceae).

This peptide is one member of the family of cyclotides, which today consist of almost 50 members. Their main character is their cyclic cystine knot; their amino acid backbone is circular and thus they lack both N- and C-terminals, and they all contain six cysteine residues involved in three disulfide bridges in a knotted arrangement. In combination with their size, ranging from 28-37 amino acid residues, these structural features renders the cyclotide peptides an extreme stability. This structural scaffold, unique for the cyclotides, has previously been shown able to mediate a variety of biological activities, such as antimicrobial and insecticidal effects.

The inventors have now surprisingly discovered that the antifouling effect against barnacles of cyclotides, and in particular cycloviolacin O2 is, in contrast to the existing antifouling agents on the market today, is non-toxic and reversible.

Thus, the present invention in its broadest aspect, which provides a novel on-growth inhibiting agent comprising a class of compounds having an on-growth inhibiting and preventing effect, is defined in claim 1.

In a further aspect of the invention, an extract from a member of the Violaceae family of plants having on-growth inhibiting and preventing properties.

In a still further aspect there is provided a method of preventing on-growth of organisms in general, including larvae, bacteria, viruses, and fungi on physical objects or on living beings.

BRIEF DESCRIPTION OF THE DRAWINGS

The invention will now be further illustrated with reference to the attached drawings wherein.

DETAILED DESCRIPTION OF THE INVENTION

Figure 1:
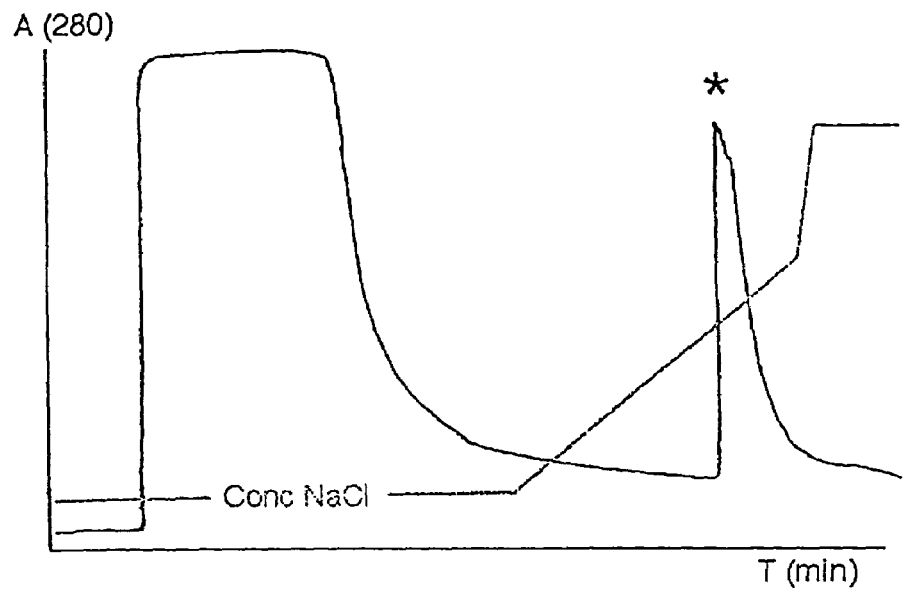
FIG. 1 illustrates the isolation by ion exchange chromatography. Cyclotides with a basic net charge was effectively captured by strong cation exchange chromatography. After elution of non charged substances, the bound peptides, here marked *, were eluted in a NaCl gradient (0-1 M). A solvent composition of 25% AcN, 0.1% TFA in water was used; the addition of AcN was shown to promote ionic interactions.

The invention is based on the discovery that a cyclopeptide designated cycloviolacin 02, extracted from the Sweet Violet, *Viola odorata* L., has an anti-fouling effect against larvae from barnacles, i.e. on-growth of barnacles on e.g. boat hulls is inhibited and even prevented, this effect being reversible.

The mechanism of action is unknown at this stage. However, without wishing to be bound by theory, it is believed that the effect may be due to a inhibition at the early stage of folding, that is prevention of the formation of a biofilm of microorganisms that preceeds settling of macroorgansims (such as barnacles). This possibility is supported by earlier observations of the antifungal and antimicrobial effect of cyclotides. Hence, it is reasonable to expand the field of the invention to areas outside the marine environmont, such as an ingredient in house paints, to prevent growth in filters and on medical equipment. The same is valid even if the mechanism is more specific, i.e. if the cyclotides act by direct binding to a molecular target (i.e. a receptor or an enzyme) which in turn repells the settling organsim(s). The latter theory is in part supported by the their reported insecticidal activity, that is that they inhibit growth of *Helicouerpa* caterpillars.

In its most general form, the invention comprises on-growth inhibiting agents comprising one or more compounds selected from the class of compounds designated as cyclotides, for the inhibition and/or prevention of on-growth of biological organisms on objects or living beings, said agent further comprising a suitable carrier medium. An embodiment of the invention comprises an extract from plants, preferably from Sweet Violet, comprising a mixture of cyclotides. In a particular embodiment, the cyclotide cycloviolacin O2 is used as the active agent. Products, in a general sense, comprising physical objects as well as living beings, such as fish, protected by the novel agent is also an aspect of the invention. Also, the method of protecting such products by applying an agent comprising the cyclotide(s), in any of the forms discussed, is part of the inventive concept.

As already discussed above, a cyclotide is a cyclic peptide which is characterized by being fairly small (the known naturally occurring cyclotides have 28-37 amino acids, although the compounds according to the invention shall not be considered limited to any particular number of amino acids), and by containing six cysteine residues forming three disulphide bridges in a knotted arrangement. A schematic representation of a general cyclotide is given in Formula I:

$C[X_1...X_a]C[X^I_1...X^I_b]C[X^{II}_1...X^{II}_c]C[X^{III}_1...X^{III}_d]C[X^{IV}_1...X^{IV}_e]C[X^V_1...X^V_f$ wherein
C is cysteine;
each of $[X_1 ... X_a]$, $[X^I_1 ... X^I_b]$, $[X^{II}_1 ... X^{II}_c]$, $[X^{III}_1 ... X^{III}_d]$, $[X^{IV}_1 ... X^{IV}_e]$, and $[X^V_1 ... X^V_f]$ represents one or more amino acid residues wherein each one or more amino acid residues within or between the sequence residues may be the same or different; and wherein
a, b, c, d, e and f represent the number of amino acid residues in each respective sequence and each of a to f may be the same or different and range from 1 to about 20;
or an analogue of said sequence (SEQ ID NO: 1

Preferably each of a to f ranges from 1 to about 10 (SEQ ID NO: 2)

In a further embodiment a, b, c, d, e and f represent the number of amino acid residues in each respective sequence and wherein a is from about 3 to about 6, b is from about 3 to about 5, c is from about 2 to about 7, d is about 1 to about 3, e is about 3 to about 6, and f is from about 4 to about 9 (SEQ ID NO: 3).

In a still further embodiment a, b, c, d, e and f represent the number of amino acid residues in each respective sequence and wherein a is about 3, b is about 4, c is from about 4 to about 7, d is about 1, e is about 4 or 5, and f is from about 4 to about 7 (SEQ ID NO: 4).

Another embodiment is provided wherein a, b, c, d, e and f represent the number of amino acid residues in each respective sequence and wherein a is about 6, b is about 4, c is 3, d is about 1, e is about 5, and f is about 8 (SEQ ID NO: 5).

As examples of cyclotides usable according to the invention, the following non-exhaustive and non-limiting listing of a number of known cyclotides is given. Thus, any of vico A, vico B, hypa A, cycloviolacin O1, cyclopsychotride A, cycloviolacin O7, circulin D, circulin E, cycloviolin C, cycloviolacin O3, cycloviolacin O9, cycloviolacin O10, cycloviolacin H1, circulin C, cycloviolin A, cycloviolin D, circulin F, circulin A, circulin B, cycloviolacin O2, cycloviolacin O4, cycloviolacin O6, cycloviolacin O11, cycloviolacin O8, cycloviolacin O5, kalata B5, cycloviolin B, varv A, kalata S, kalata B1, kalata B4, varv E, cycloviolacin O12, varv D, varv C, varv B, varv G, varv H, kalata B2, kalata B3, kalata B6, varv F, kalata B7, alone or in combination can be used in the on-growth inhibiting agent according to the invention.

The actual amino acid sequence for these compounds can be found in Table 4, in the doctoral thesis by Ulf Göransson, "Macrocylic Polypeptides from Plants" (ACTA UNIVERSITATIS UPSALIENSIS UPPSALA 2002), page 36.

The particular peptide tested in the Examples below, cycloviolacin O2, belongs to the family of cyclic plant peptides recently named cyclotides. It was isolated from the dried aerial part of the plant *Viola odorata* through already established techniques for cyclotide isolation in combination with strong cation exchange chromatography. The latter was shown to be an efficient complementary method for capture of cyclotides containing a positive net charge (FIG. 1). The rapidly growing family today consists of about 50 different peptides, mainly isolated from the Violaceae and Rubiaceae plant families.

The number of cyclotides known to occur in the family of Violaceae, and their high degree of sequence homology, made molecular weight alone insufficient for absolute identification after isolation of the peptide. Hence, it was modified by introduction of charged cleavage sites on the cysteines, followed by enzymatic digestion to produce peptide fragments suitable for sequencing by MS. After aminopropylation and tryptic cleavage the major part of the sequence was obtained. For full coverage, possible cleavage sites were constrained to modified cysteines only: trypsin was exchanged for endoproteinase LysC to prevent cleavage after the arginine residue, native lysine cleavage sites were protected by acetylation, and finally, cysteines were aminoethylated instead of aminopropylated to better suit the chosen enzyme. After this, the full sequence could be determined to cyclo-(VWIPCISSAIGC-SCKSKVCYRNGIPCGESC) (SEQ ID NO: 6), unambiguously identifying the peptide as the previously reported cycloviolacin O2.

A vide variety of effects has previously been ascribed to the cyclotides, including antimicrobial, HIV-inhibitory, trypsin inhibitory and cytotoxic ones. Their function within the plant however, have not yet been fully elucidated, but probably they are involved in the host defence system. This conjecture was recently supported by Jennings and coworkers, that showed potent insecticidal activities of the cyclotide kalata B1; growth and development of the insect larvae (from *Helicoverpa punctigera*) was shown to be greatly affected in a feeding trial. While this activity seems intriguingly similar in aspect to cycloviolacin O2:s ability to inhibit cyprides from fouling; the insect larvae also showed an increase in mortality over time. Though, it may be hypothesized that there might be a common mechanism behind the two findings, and that the difference instead lies in the surrounding environment and its influence to the test organisms ability to give off the peptide; the marine milieu simulated in the antifouling bioassay, is ideally suited to maintain equilibriums of water soluble compounds such as peptides. Indeed, the fact that the antifouling effect is reversible show that such an equilibrium does exist in our system. Hence, the reason that the peptide can be solubilised in the surrounding water may be the simple explanation to the difference in toxicity between these two seemingly related activities.

All of the members of the cyclotide family contain around 30 amino acid residues, organised in the characteristic cyclic cystine knot motif; a head-to-tail cyclised amide backbone further stabilised by three intramolecular disulfide bridges. Through slight variations in the sequences between cysteines—the loops—the plant provide itself with a library of different peptides. This variety of cyclotides may be used to further explore the antifouling effect reported here, as it enables detailed structure activity studies. Such studies may be further expanded by the use of synthetic chemistry developed for cyclotides, to identify which parts or regions of the peptide that is important for activity. Likewise, a similar approach may be used to optimise the sequence to suit a specific formulation or use, for example to covalently bind the cyclotide directly to a surface or into an antifouling paint.

To our knowledge, this is the first disclosure of an evaluation of a natural product from a terrestrial source against fouling barnacles. Moreover, the tested substance represents a class and size of molecules—peptides—that generally are considered non-attractive due to their instability. However, we have isolated a peptide belonging to the cyclotide family, recognised as one of the most stable peptide structures known, with a potency in the same range as TBTO. A complete inhibition of fouling was observed at a concentration of 0.25 µM [EC50 values for TBTO, 0.09 µg ml$^{-1}$ or 0.15 µM]. In addition, cycloviolacin O2 showed a distinct advantage compared to both TBTO and any other commercially used antifouling agent of today; the effect is non toxic and reversible.

To conclude, we have shown that the search for antifouling agents may be expanded to natural products from terrestrial sources, exemplified here by the potent activity of the cyclic peptide cycloviolacin O2.

Anti-Fouling Products Containing the Class of Inventive Compounds

The novel class of compounds according to the invention can suitably be used in anti-fouling products for underwater use and such products can be prepared by conventional methods.

Cyclotides as defined in the claims can for example be mixed with a binding agent such as an organopolysiloxane, e.g. a low molecular mass alkoxy-functional silicone resin, a silicone rubber or an organosilicon copolymer.

An anti-fouling composition comprising cyclotides according to the invention and an organopolysiloxane can additionally comprise inorganic pigments, organic pigments, dyes (which are preferably insoluble in salt water) and/or conventional auxiliaries such as fillers, solvents, plasticizers, catalysts, inhibitors, tackifiers, coating additives and/or common dispersion auxiliaries.

Other examples of anti-fouling compositions that are meant for use under water and that can be used with anti-fouling agents according to the present invention, are disclosed in U.S. Pat. No. 6,245,784-B1, U.S. Pat. No. 6,217,642-B1, U.S. Pat. No. 6,291,549-B1, U.S. Pat. No. 6,211,172-B1 and U.S. Pat. No. 6,172,132-B1.

The final anti-fouling products could be used for underwater structures, e.g. in plumbing ports of nuclear power stations, at ocean facilities such as bayshore roads, undersea tunnels, port facilities, and in canals or channels, machinery operated by the power of sea motion (waves), such as power plants. The agents according to the invention could also be used for coating marine vessels, fishing gear (rope, fishing net or the like).

The anti-fouling coating compositions can be applied either directly to the surface of vessel hulls and underwater structures or applied to the surface of vessel hulls and underwater structures pre-coated with undercoating material such as rust preventive and a primer.

The anti-fouling coating compositions may also be used to repair surfaces of vessel hulls and underwater structures previously coated with a conventional anti-fouling paint or anti-fouling coating composition.

Other structures and devices that can be protected by the novel agents are exemplified by membranes, pumps, filters etc employed in the biotechnology process industry.

Further fields of use that are possible are the protection of medical equipment from the on-growth of bio film, i.e. bacterial and/or microbial adhesion on the surface of devices such as surgical instruments, tubing in contact with body fluids etc.

It is also conceivable to protect fish in fish breeding plants form on-growth of unwanted species, e.g. bacteria and/or other organisms having a pathogenic effect on the fish, by the application of an agent according to the invention, either directly to the body of the animal, or by administration in the water or with the fodder. Possibly, also other animals such as cattle could be protected from infestation or attacks by vermins.

The present invention will now be described by way of examples, based on extraction of active compounds from Sweet Violet, *Viola odorata* L.

EXAMPLES

General Procedures.

HPLC (cation exchange and RP) was done on a Äkta Basic system (Amersham Biosciences, Uppsala, Sweden). Mass spectrometry was done by nanospray-ion trap MS [Protana's NanoES source (MDS Protana A/S, Odense, Denmark) mounted on a LCQ (Thermo Finningan, San Jose, USA)] operated in the positive ion mode. Samples were sprayed using a 60% MeOH, 1% HOAc in water; the capillary temperature was set at 150° C. and the spray voltage at 0.5 kV. For MS/MS sequencing the relative CID was typically set at 35%. Unless otherwise stated, average masses were used and given as [M].

Isolation of Cycloviolacin O2.

Dried and grinded plant material (*Viola odorata* L., obtained from Galke, Gittelde, Germany) was defatted with dichloromethane before the main extraction was carried out using 50% aqueous ethanol. This extract was concentrated in vacuo (i.e. all EtOH was removed) then the acidified extract was filtered through polyamide to remove tannins. This is referred to as Fraction P. Subsequently this extract was partitioned between H$_2$O and n-BuOH. So far, the isolation procedure was carried out according to Claeson et al in "Fractionation protocol for the isolation of polypeptides from plant biomass", J. Nat. Prod. 61, 77-81, and Broussalis et al in "First cyclotide from Hybanthus (Violaceae)", Phytochemistry 58, 47-51. The BuOH fraction was then evaporated, and redissolved in 25% acetonitrile, 0.1% trifluoroacetic acid in water before pumped through a Vydac sulfonic acid polymeric strong cation exchange column (400VHP575, 5 µm, 7.5 mm ID×50 mm) at a flow rate of 1 ml/min, until the binding sites of the gel were saturated. Bound substances were then eluted with a salt gradient, ranging from 0 to 1M NaCl. The peak (referred to as Fraction I) eluting in the salt gradient was collected (FIG. 1), and analysed by RP-HPLC and MS, and was found to contain a mixture of peptides. The major peptide was then isolated by means of RP-HPLC in an analogous way as described in the article by Broussalis et al and in Göransson et al, "Seven novel macrocyclic polypeptides from *Viola arvensis*", J. Nat. Prod. 62, 283-6.

LC/MS Analysis of Fraction P of *Viola odorata*.

Figure 6:
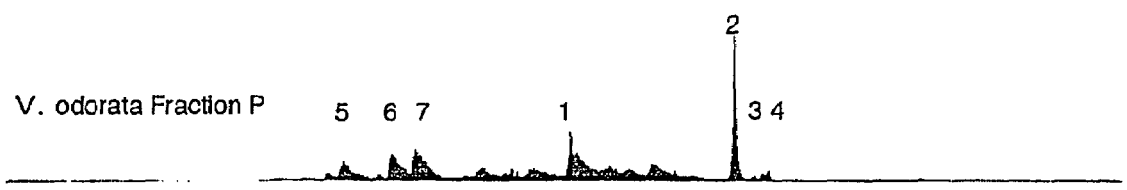
FIG. 6 illustrates LC/MS analysis of Fraction P of *Viola odorata*.

The fraction contains a mixture of cyclotides, one of the major components is cycloviolacin O2 which was tested as a pure compound. However, results from testing the fraction itself reveals that a similar activity may be found for other members of the cyclotide family. An LC/MS analysis was performed on this extract, and is shown in FIG. 6. Some of the identified cyclotides are marked in the chromatogram as folloes: cycloviolacin O2 (marked as 1). These are kalataS/varv peptide A (2); varv peptide D (3); varv peptide E (4); cycloviolacin O9 (5); cycloviolacin O3 (6); cycloviolacin O7 (7), which represent a wide variety of cyclotide sequences.

Aminopropylation/aminoethylation.

Peptide (1-5 nmol) was reduced with dithioerythritol (DTE, 390 nmol) in 0.25 M Tris-HCl containing 1 mM EDTA and 6 M guanidine-HCl (pH 8.5; 24° C.; 1 h). Reduced peptide was then alkylated by the addition of 25 times the amount bromopropylamine/bromoethylamine versus DTE (9.75 µmol) dissolved in 10 ul of the Tris-HCl buffert. The reaction was then incubated overnight (37° C.), after which it was terminated by injection on RP-HPLC.

Acetylation of Lysines.

Dry peptide (1 nmol) was dissolved in 20 µl 50 mM NH4HCO3. To this, 50 µl of acetic anhydride in methanol (⅓) was added. After 1 hour incubation at room temperature, the mixture was lyophilized to dryness.

Larval Bioassay.

The brood stock of adult barnacles (*B. improvisus*, Darwin 1854) were allowed to settle on Plexi glass® panels in the sea on a raft outside Tjärnö Marine Biological Laboratory (58°53'N, 11°8'E). Cleaned from epiphytes they were brought to the laboratory and immediately placed in trays with running seawater (salinity 32±1%). When regularly fed, with nauplii of *Artemia salina*, *B. improvisus* will spawn throughout the year. For larval rearing we used the method according to Berntsson et al., described in "Reduction of barnacle recruitment on micro-textured surfaces: Analysis of effective topographic characteristics and evaluation of skin friction", Biofouling 16, 245-261. The experiment for the evaluation of the effect on settlement and mortality was performed using polystyrene Petri dishes (ø 48 mm) to which 10 ml of the peptide dissolved to different concentrations in filtered seawater (0.2 µm, 32±1‰) was added. Competent cyprids (20±2 ind.) were added to each dish in four replicates and dishes with filtered seawater served as controls. Dishes were maintained for 3-4 days in room temperature after which they were examined under a stereo microscope for attached and metamorphosed individuals and also, for dead cyprids.

Reversibility Test.

Half of the number of cyprids in each petri dish incubated at the highest tested concentration, 2.5 µM, were moved to a petri dish containing 10 ml of fresh seawater. These petridishes, as well as the original ones incubated at this concentration were examined as described above after five days of incubation.

Statistical Method

Results are reported as means±standard error and using 1-factor analysis of variance (ANOVA).

Example 1

Isolation and identification of cycloviolacin O2.

Extraction of plant material and isolation of cycloviolacin O2 was carried out as previously described, with the exception of the use of strong cation exchange chromatography, which effectively captured positively charged cyclotides (FIG. 1). The peak eluting in the salt gradient was collected, and analysed by RP-HPLC and MS, and was found to contain a mixture of peptides. The major peptide was then isolated by means of RP-HPLC, in analogy with previous isolations of cyclotides.

The molecular weight of the isolated peptide was determined to 3140.4 Da, congruent with the molecular weight of the earlier reported cycloviolacin O2 (calculated 3140.8). To unambiguously establish its identity, the peptide was digested with trypsin after converting the cysteines of the reduced peptide into its aminopropylated and its acetylated and aminoethylated derivatives. Obtained fragments were then sequenced by MS/MS.

After aminopropylation and tryptic cleavage, the sequence of 26 out of 31 amino acids in four identified fragments were successfully determined (sorted after masses, all cysteines converted to their aminopropylated derivatives): VCYR (SEQ ID NO: 7) [597.5 (MH+)] VWIPC (SEQ ID NO: 8) [674.4 (MH+)]; ISSAIGC (SEQ ID NO: 9) [707.5 (MH+)] and NGIPCGESC (SEQ ID NO: 10) [994.5 (MH+)]. The remaining five residues were identified first after acetylation, to protect this particular fragment from internal cleavage, followed by aminoethylation and tryptic cleavage to KSKVC (SEQ ID NO: 11) [691.3, (MH+)]. Together, these MS data gave the following sequence: cyclo-(VWIPCISSAIGCSCK-SKVCYRNGIPCGESC) (SEQ ID NO: 6)

Example 2

On-Growth Inhibiting ("Antifouling") Effect of Cycloviolacin O2.

Figure 2:
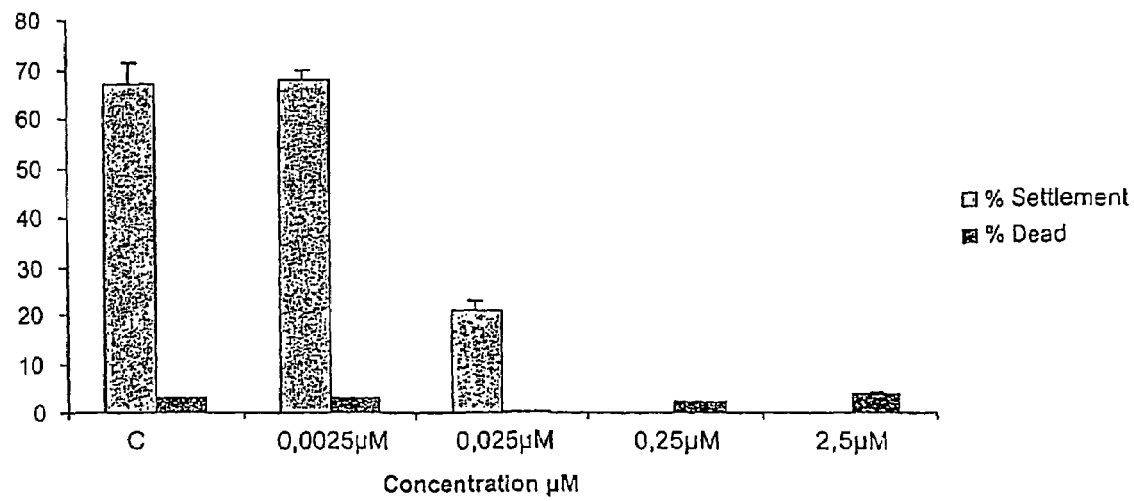
FIG. 2 shows the antifouling effect of cycloviolacin O2. The settlement was inhibited in a dose-dependent manner. At 0.25 µM cycloviolacin O2 there was a complete inhibition of settlement. No one of the tested concentrations showed an increase in mortality compared to the control (saltwater only). All concentrations were tested in quadruplicates.

The effect of cycloviolacin O2 on settlement and mortality of *B. improvisus* is shown in FIG. 2. The settlement was inhibited in a dose-dependent manner; at the lowest tested concentration (0.0025 µM), the degree of settlement was the same as in the control (saltwater only) with 68±3% and 67±3% settlement respectively; at 0.025 µM only 21±0.5% of the cyprids settled; and at 0.25 µM cycloviolacin O2 there was a complete inhibition of settlement.

The antifouling effect is non-toxic and reversible.

Figure 3:
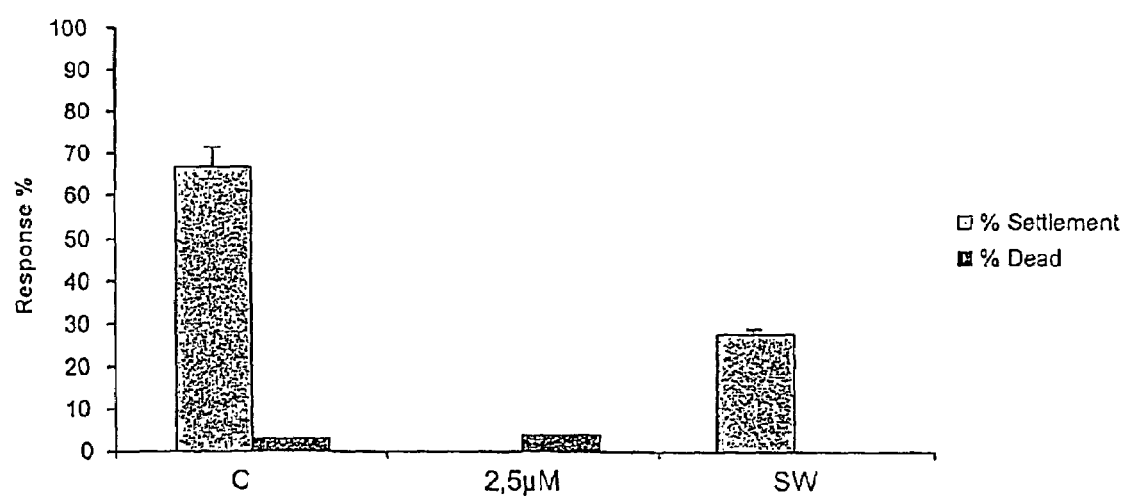
FIG. 3 demonstrates the reversibility test. Compared to the control, a lower percentage of settlement was seen of cypris transferred from 2.5 µM cycloviolacin O2. This is however a normal behaviour after long incubation times, in this case 3+5 days, and may be explained by exhaustion. No increase in mortality was observed. All concentrations were tested in quadruplicates.

No increase in mortality could be detected even at the highest tested concentration (2.5 µM), compared to the control (FIG. 2). Cyprids incubated at this concentration were then moved into petri dishes containing fresh sea water (without cycloviolacin O2), where they regained their normal behaviour, that is to settle, as shown in FIG. 3. After five days of incubation in this solution, 27% of the transferred cyprids had settled. No increase in mortality was observed.

Example 3

On-Growth Inhibiting ("Antifouling") Effects of *Viola odorata* extracts

Figure 4:
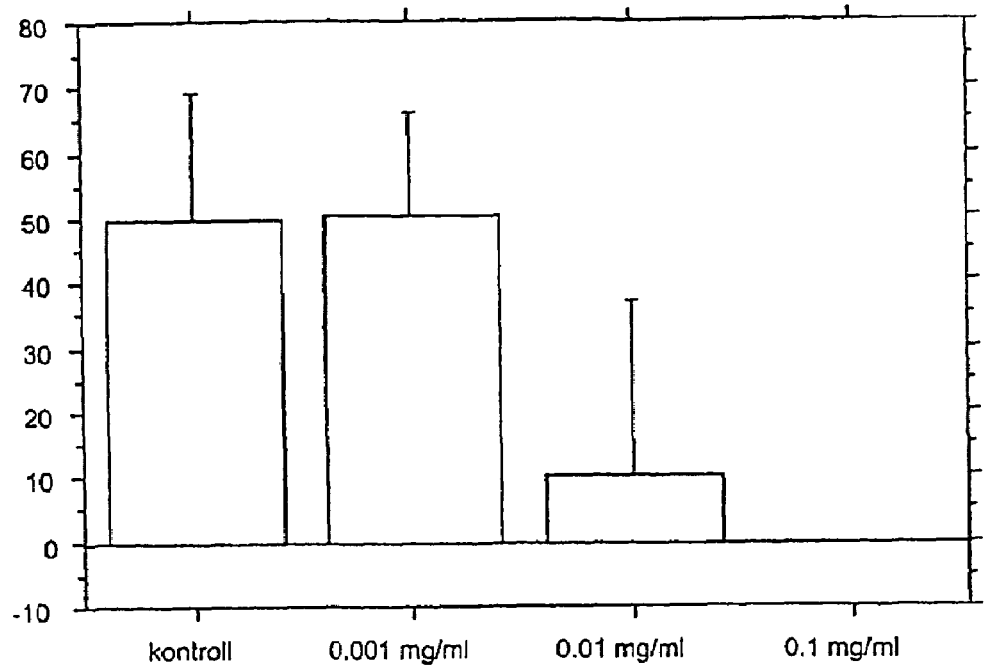
FIG. 4 illustrates effect on settlement of Fraction P from an extraction process performed on Sweet Violet.
Figure 5:
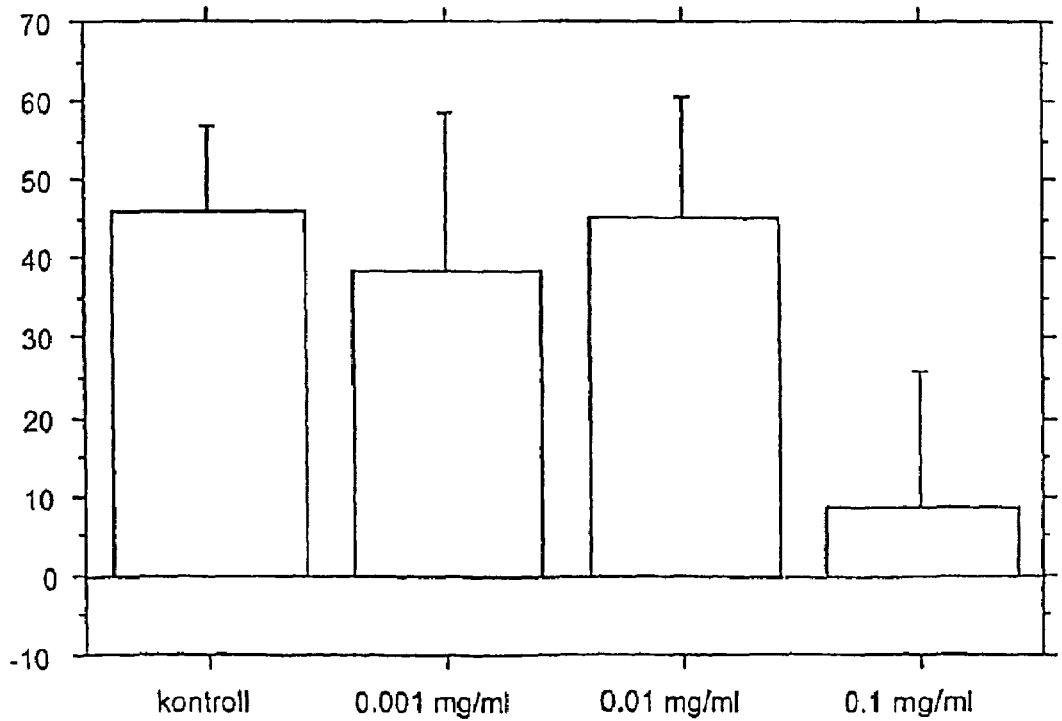
FIG. 5 illustrates effect on settlement of Fraction I from Sweet Violet.

Extraction and fractionation of plant material was carried out as previously described (Claeson et al., 1998; Göransson et al., 1999; Broussalis et al.,. 2001). The peptide enriched crude extract obtained following the established fractionation protocol (i.e. Fraction P) was subjected to cation exchange chromatography, to capture the positively charged cyclotides (Fraction I). Both Fraction P and I were tested for antifouling effect (settling and mortality) of *Balanus improvisous* (FIGS. 4 and 5, respectively). When testing Fraction P, settlement was inhibited in a dose-dependent manner; at lowest concentration (0.001 mg/ml), the degree of settlement was the same as in the control (saltwater only); and at 0.1 mg/ml there was a complete inhibition of settlement. Fraction I also inhibited settlement, but only at 0.1 mg/ml. Fraction I was further purified by means of RP-HPLC and the major cyclotide was isolated (i.e. cycloviolacin O2). The inhibition on settlement of cycloviolacin O2 is dose-dependent and at 0.25 µM there was a complete inhibition.

Example 4

A Field Test was Performed as Follows:

Fraction P of *V. odorata* was dissolved in a marine paint (SPF, Loutrec, Lidingö, Sweden) in two different concentrations, 1% and 0.1% (w/w). Plexiglass plates (PMMA, polymethylmetacrylate) of 11×11 cm were then coated with 2 ml in a single layer of respective paint. A set of plates were painted with paint only and served as controls, and all experiments were done in quadruplicates. After drying, the plates were randomly fixed to ropes, attached in one end to a buoy and in the other to a weight, which were deployed in the sea in a bay outside TjärnöMarine Biological Laboratory (58°53'N,11°8'E) in August 2003. A set of 4 plates (of each concentration and control) were brought to the lab after 4 and 8 weeks, respectively, and examined for settled barnacles. No settling could be observed for the dishes coated with paint containing Fraction P.

The invention claimed is:

1. A method of inhibiting marine fouling of underwater structures, comprising: applying a coating composition comprising
  i) at least one cyclotide is selected from the group consisting of SEQ ID NO: 3, SEQ ID NO: 4, and SEQ ID NO: 5, and
  ii) a binding agent.

2. The method according to claim 1, wherein the cyclotide is SEQ ID NO: 3.

3. The method according to claim 1, wherein the cyclotide is SEQ ID NO: 4.

4. The method according to claim 1, wherein the cyclotide is SEQ ID NO:5.

5. A method of inhibiting marine fouling of underwater structures, comprising: applying a coating composition comprising
  i) at least one cyclotide selected from the group consisting of: vico A, vico B, hypa A, cycloviolacin O1, cyclopsychotride A, cycloviolacin O7, circulin D, circulin E, cycloviolin C, cycloviolacin O3, cycloviolacin O9, cycloviolacin O10, cycloviolacin H1, circulin C, cycloviolin A, cycloviolin D, circulin F, circulin A, circulin B, cycloviolacin O2, cycloviolacin O4, cycloviolacin O6, cycloviolacin O11, cycloviolacin O8, cycloviolacin O5, kalata B5, cycloviolin B, varv A, kalata S, kalata B1, kalata B4, varv E, cycloviolacin O12, varv D, varv C, varv B, varv G, varv H, kalata B2, kalata B3, kalata B6, varv F, kalata B7, and combinations thereof, and
  ii) a binding agent.

6. The method according to claim 5, wherein the cyclotide is cycloviolacin O2.

7. The method according to claim 6, wherein the cyclotide is obtained from Sweet Violet.

8. A method of inhibiting fouling of underwater structures by marine organisms comprising applying a coating composition: at least one cyclotide selected from the group consisting of: vico A, vico B, hypa A, cycloviolacin O1, cyclopsychotride A, cycloviolacin O7, circulin D, circulin E, cycloviolin C, cycloviolacin O3, cycloviolacin O9, cyclovi olacin O10, cycloviolacin H1, circulin C, cycloviolin A, cycloviolin D, circulin F, circulin A, circulin B, cycloviolacin O2, cycloviolacin O4, cycloviolacin O6, cycloviolacin O11, cycloviolacin O8, cycloviolacin O5, kalata B5, cycloviolin B, varv A, kalata S, kalata B1, kalata B4, varv E, cycloviolacin O12, varv D, varv C, varv B, varv G, varv H, kalata B2, kalata B3, kalata B6, varv F, kalata B7, and combinations thereof.

9. The method according to claim 8, wherein the cyclotide is cycloviolacin O2.

* * * * *

SEQUENCE LISTING

```
<160> NUMBER OF SEQ ID NOS: 11

<210> SEQ ID NO 1
<211> LENGTH: 126
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(21)
<223> OTHER INFORMATION: Variable amino acid and this region may
      encompass 1 to 20 residues
<220> FEATURE:
<221> NAME/KEY: MOD_RES
<222> LOCATION: (23)..(42)
<223> OTHER INFORMATION: Variable amino acid and this region may
      encompass 1 to 20 residues
<220> FEATURE:
<221> NAME/KEY: MOD_RES
<222> LOCATION: (44)..(63)
<223> OTHER INFORMATION: Variable amino acid and this region may
      encompass 1 to 20 residues
<220> FEATURE:
<221> NAME/KEY: MOD_RES
<222> LOCATION: (65)..(84)
<223> OTHER INFORMATION: Variable amino acid and this region may
      encompass 1 to 20 residues
<220> FEATURE:
<221> NAME/KEY: MOD_RES
<222> LOCATION: (86)..(105)
<223> OTHER INFORMATION: Variable amino acid and this region may
      encompass 1 to 20 residues
<220> FEATURE:
<221> NAME/KEY: MOD_RES
<222> LOCATION: (107)..(126)
<223> OTHER INFORMATION: Variable amino acid and this region may
      encompass 1 to 20 residues

<400> SEQUENCE: 1

Cys Xaa Xaa Xaa Xaa Xaa Xaa Xaa Xaa Xaa Xaa Xaa Xaa Xaa Xaa Xaa
 1               5                  10                  15

Xaa Xaa Xaa Xaa Cys Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Cys Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Cys Xaa
    50                  55                  60

Xaa Xaa Xaa Xaa Xaa Xaa Xaa Xaa Xaa Xaa Xaa Xaa Xaa Xaa Xaa Xaa
 65                 70                  75                  80

Xaa Xaa Xaa Xaa Cys Xaa Xaa Xaa Xaa Xaa Xaa Xaa Xaa Xaa Xaa Xaa
            85                  90                  95
```

Xaa Xaa Xaa Xaa Xaa Xaa Xaa Xaa Xaa Cys Xaa Xaa Xaa Xaa Xaa Xaa
                100                 105                 110

Xaa Xaa Xaa Xaa Xaa Xaa Xaa Xaa Xaa Xaa Xaa Xaa Xaa Xaa
        115                 120                 125

<210> SEQ ID NO 2
<211> LENGTH: 66
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(11)
<223> OTHER INFORMATION: Variable amino acid and this region may
      encompass 1 to 10 residues
<220> FEATURE:
<221> NAME/KEY: MOD_RES
<222> LOCATION: (13)..(22)
<223> OTHER INFORMATION: Variable amino acid and this region may
      encompass 1 to 10 residues
<220> FEATURE:
<221> NAME/KEY: MOD_RES
<222> LOCATION: (24)..(33)
<223> OTHER INFORMATION: Variable amino acid and this region may
      encompass 1 to 10 residues
<220> FEATURE:
<221> NAME/KEY: MOD_RES
<222> LOCATION: (35)..(44)
<223> OTHER INFORMATION: Variable amino acid and this region may
      encompass 1 to 10 residues
<220> FEATURE:
<221> NAME/KEY: MOD_RES
<222> LOCATION: (46)..(55)
<223> OTHER INFORMATION: Variable amino acid and this region may
      encompass 1 to 10 residues
<220> FEATURE:
<221> NAME/KEY: MOD_RES
<222> LOCATION: (57)..(66)
<223> OTHER INFORMATION: Variable amino acid and this region may
      encompass 1 to 10 residues

<400> SEQUENCE: 2

Cys Xaa Xaa Xaa Xaa Xaa Xaa Xaa Xaa Xaa Cys Xaa Xaa Xaa Xaa
  1               5                  10                  15

Xaa Xaa Xaa Xaa Xaa Xaa Cys Xaa Xaa Xaa Xaa Xaa Xaa Xaa Xaa
            20                  25                  30

Xaa Cys Xaa Xaa Xaa Xaa Xaa Xaa Xaa Xaa Xaa Cys Xaa Xaa Xaa
        35                  40                  45

Xaa Xaa Xaa Xaa Xaa Xaa Xaa Cys Xaa Xaa Xaa Xaa Xaa Xaa Xaa
    50                  55                  60

Xaa Xaa
 65

<210> SEQ ID NO 3
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(7)
<223> OTHER INFORMATION: Variable amino acid and this region may
      encompass 3 to 6 residues
<220> FEATURE:
<221> NAME/KEY: MOD_RES
<222> LOCATION: (9)..(13)

<223> OTHER INFORMATION: Variable amino acid and this region may
      encompass 3 to 5 residues
<220> FEATURE:
<221> NAME/KEY: MOD_RES
<222> LOCATION: (15)..(21)
<223> OTHER INFORMATION: Variable amino acid and this region may
      encompass 2 to 7 residues
<220> FEATURE:
<221> NAME/KEY: MOD_RES
<222> LOCATION: (23)..(25)
<223> OTHER INFORMATION: Variable amino acid and this region may
      encompass 1 to 3 residues
<220> FEATURE:
<221> NAME/KEY: MOD_RES
<222> LOCATION: (27)..(32)
<223> OTHER INFORMATION: Variable amino acid and this region may
      encompass 3 to 6 residues
<220> FEATURE:
<221> NAME/KEY: MOD_RES
<222> LOCATION: (34)..(42)
<223> OTHER INFORMATION: Variable amino acid and this region may
      encompass 4 to 9 residues

<400> SEQUENCE: 3

Cys Xaa Xaa Xaa Xaa Xaa Xaa Cys Xaa Xaa Xaa Xaa Xaa Cys Xaa Xaa
 1               5                  10                  15

Xaa Xaa Xaa Xaa Xaa Cys Xaa Xaa Xaa Cys Xaa Xaa Xaa Xaa Xaa Xaa
            20                  25                  30

Cys Xaa Xaa Xaa Xaa Xaa Xaa Xaa Xaa Xaa
        35                  40

<210> SEQ ID NO 4
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Variable amino acid
<220> FEATURE:
<221> NAME/KEY: MOD_RES
<222> LOCATION: (6)..(9)
<223> OTHER INFORMATION: Variable amino acid
<220> FEATURE:
<221> NAME/KEY: MOD_RES
<222> LOCATION: (11)..(17)
<223> OTHER INFORMATION: Variable amino acid and this region may
      encompass 4 to 7 residues
<220> FEATURE:
<221> NAME/KEY: MOD_RES
<222> LOCATION: (19)
<223> OTHER INFORMATION: Variable amino acid
<220> FEATURE:
<221> NAME/KEY: MOD_RES
<222> LOCATION: (21)..(25)
<223> OTHER INFORMATION: Variable amino acid and this region may
      encompass 4 to 5 residues
<220> FEATURE:
<221> NAME/KEY: MOD_RES
<222> LOCATION: (27)..(33)
<223> OTHER INFORMATION: Variable amino acid and this region may
      encompass 4 to 7 residues

<400> SEQUENCE: 4

Cys Xaa Xaa Xaa Cys Xaa Xaa Xaa Xaa Cys Xaa Xaa Xaa Xaa Xaa Xaa
 1               5                  10                  15

Xaa Cys Xaa Cys Xaa Xaa Xaa Xaa Xaa Cys Xaa Xaa Xaa Xaa Xaa Xaa
            20                  25                  30

Xaa

```
<210> SEQ ID NO 5
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(7)
<223> OTHER INFORMATION: Variable amino acid
<220> FEATURE:
<221> NAME/KEY: MOD_RES
<222> LOCATION: (9)..(12)
<223> OTHER INFORMATION: Variable amino acid
<220> FEATURE:
<221> NAME/KEY: MOD_RES
<222> LOCATION: (14)..(16)
<223> OTHER INFORMATION: Variable amino acid
<220> FEATURE:
<221> NAME/KEY: MOD_RES
<222> LOCATION: (18)
<223> OTHER INFORMATION: Variable amino acid
<220> FEATURE:
<221> NAME/KEY: MOD_RES
<222> LOCATION: (20)..(24)
<223> OTHER INFORMATION: Variable amino acid
<220> FEATURE:
<221> NAME/KEY: MOD_RES
<222> LOCATION: (26)..(33)
<223> OTHER INFORMATION: Variable amino acid

<400> SEQUENCE: 5

Cys Xaa Xaa Xaa Xaa Xaa Xaa Cys Xaa Xaa Xaa Xaa Cys Xaa Xaa Xaa
 1               5                  10                  15

Cys Xaa Cys Xaa Xaa Xaa Xaa Xaa Cys Xaa Xaa Xaa Xaa Xaa Xaa Xaa
            20                  25                  30

Xaa

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Trp Ile Pro Cys Ile Ser Ser Ala Ile Gly Cys Ser Cys Lys Ser
 1               5                  10                  15

Lys Val Cys Tyr Arg Asn Gly Ile Pro Cys Gly Glu Ser Cys
            20                  25                  30

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Cys Tyr Arg
 1

<210> SEQ ID NO 8
<211> LENGTH: 5
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 8

Val Trp Ile Pro Cys
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Ser Ser Ala Ile Gly Cys
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asn Gly Ile Pro Cys Gly Glu Ser Cys
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Ser Lys Val Cys
1               5
```